United States Patent [19]

Frantzen et al.

[11] Patent Number: 5,728,131
[45] Date of Patent: Mar. 17, 1998

[54] COUPLING DEVICE AND METHOD OF USE

[75] Inventors: John J. Frantzen, Copperopolis; Geoffrey A. Orth, La Granada, both of Calif.

[73] Assignee: Endotex Interventional Systems, Inc., Menlo Park, Calif.

[21] Appl. No.: 489,650

[22] Filed: Jun. 12, 1995

[51] Int. Cl.⁶ .................................................... A61B 17/00
[52] U.S. Cl. ........................ 606/194; 606/191; 623/1; 623/12
[58] Field of Search ............................ 606/191, 192, 606/194, 200, 151; 623/1, 11, 12

[56] References Cited

U.S. PATENT DOCUMENTS

| | | |
|---|---|---|
| 3,657,744 | 4/1972 | Ersek . |
| 3,683,926 | 8/1972 | Suzuki .................................. 128/334 R |
| 4,787,899 | 11/1988 | Lazarus . |
| 4,938,740 | 7/1990 | Melbin . |
| 4,957,508 | 9/1990 | Kaneko et al. ............................ 623/12 |
| 4,969,890 | 11/1990 | Sugita et al. . |
| 4,994,071 | 2/1991 | MacGregor . |
| 5,035,706 | 7/1991 | Giantureo et al. . |
| 5,064,435 | 11/1991 | Porter . |
| 5,078,726 | 1/1992 | Kreamer . |
| 5,084,064 | 1/1992 | Barak et al. ............................ 623/1 |
| 5,102,417 | 4/1992 | Palmaz . |
| 5,104,399 | 4/1992 | Lazarus ............................ 623/1 |
| 5,104,404 | 4/1992 | Wolff . |
| 5,195,984 | 3/1993 | Schatz . |
| 5,207,695 | 5/1993 | Trout, III ............................ 606/153 |
| 5,275,622 | 1/1994 | Lazarus et al. ............................ 623/1 |
| 5,282,823 | 2/1994 | Schwartz et al. . |
| 5,282,824 | 2/1994 | Gianturco . |
| 5,382,261 | 1/1995 | Palmaz . |
| 5,443,497 | 8/1995 | Venbrux ............................ 606/191 |
| 5,449,382 | 9/1995 | Dayton ............................ 623/1 |
| 5,522,881 | 6/1996 | Lentz ............................ 606/191 |

FOREIGN PATENT DOCUMENTS

| | | | |
|---|---|---|---|
| 0646365 | 4/1995 | European Pat. Off. | A61F 2/06 |
| WO 88/06865 | 9/1988 | WIPO | A61B 11/00 |
| WO 93/20757 | 10/1993 | WIPO | A61B 17/11 |
| WO 94/06372 | 3/1994 | WIPO | A61F 2/04 |
| WO 96/14808 | 5/1996 | WIPO | A61F 2/02 |

*Primary Examiner*—Jeffrey A. Schmidt
*Attorney, Agent, or Firm*—Fish & Neave

[57] ABSTRACT

A coupler is provided for connecting a stent and a vascular graft for repairing aneurysms. An intravascular stent is connected to a vascular graft by a coupler having a high degree of elasticity so that the stent-coupler-graft assembly can be implanted to repair a body passageway, including aortic aneurysms.

18 Claims, 5 Drawing Sheets

COUPLING DEVICE AND METHOD OF USE

BACKGROUND OF THE INVENTION

1. Field of the Invention

This invention relates generally to endoprostheses, and more particularly concerns intraluminal grafts and stents for placement in an area of a body lumen that has been weakened by damage or disease, such as by aneurysm of the abdominal aorta.

2. Description of Related Art

An abdominal aortic aneurysm ("AAA") is an abnormal dilation of the arterial wall of the aorta in the region of the aorta that passes through the abdominal cavity. The condition most commonly results from atherosclerotic disease. Frequently, abdominal aortic aneurysms are dissecting aneurysms that are formed when there is a tear or fissure in the arterial lining or wall through which blood is forced and where it eventually clots, forming a thrombosis that swells and weakens the vessel. Abdominal aortic aneurysms do not cause pain, but are easily detected in a thorough physical examination. If the aneurysm is not detected and treated, it is likely to rupture and cause massive hemorrhaging fatal to the patient.

Treatment of AAA's typically takes the form of arterial reconstructive surgery. One such method is bypass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a biocompatible material that is compliant and thin-walled. Synthetic fibers such as those manufactured under the trademarks DACRON or TEFLON have been found to be suitable for the construction of the graft. Studies have shown that the mortality rate associate with this surgical procedure is favorable (less than 5%) when it is performed prior to rupture of an aneurysm. However, patients having an AAA are typically over 65 year of age, and often have other chronic illnesses which increase the risk of perioperative or post-operative complications. Those patients thus are not ideal candidates for this type of major surgery. Further, it has been pointed out that this procedure is not often successfully resorted to after an aneurysm has ruptured (the mortality rate increases to over 65%) because of the extensiveness of the surgery and the time required to prepare a patient for it.

Another procedure developed as an alternative to conventional surgical methods involves placement of a graft at the site of the aneurysm. However, the graft is deployed there by being routed through the vascular system carried by a catheter, wire or other device suitable for negotiating the vasculature. The graft and its deployment system often are introduced into the blood stream percutaneously with a femoral approach and the entire procedure can be performed using local rather than general anesthesia. Once the graft has been positioned at the aneurysm, it is disengaged from the delivery system and can be affixed to the aortic wall both distally and proximally of the aneurysm. For this purpose, grafting systems usually include fixation means such as staples or hooks which can be manipulated and driven into the intima of the vessel via some mechanical feature of the system, or by some physical process, such as expansion of the graft through application of pressure or temperature change. To avoid premature detachment of the graft and to prevent the attachment elements from damaging the vessels or halting the forward movement of the system while the graft is being routed to the treatment site, the systems often are provided with a feature such as a capsule or a sheath that protects and contains the graft until such time as deployment is desired.

Once the graft is in place, it is positioned in the vessel spanning the site of the aneurysm such that the walls of the graft are generally parallel to the walls of the affected area of the aorta. The aneurysm thus is excluded from the circulatory system by the graft rather than being resected altogether.

Grafting systems are known that include what is commonly referred to as an attachment system for deploying the graft. The attachment system is typically a tubular device which is fitted inside and is generally coaxial with the graft, and can extend beyond either or both of the proximal and distal ends of the graft. The attachment system often has a lattice-like or open weave structure, which provides it with flexibility and which promotes rapid endothelial tissue growth through the structure once the graft has been deployed. It may be provided with additional hook-like elements for penetration of the vessel walls for attachment of the graft to the aorta, or those hook-like elements may be provided on the graft itself. Graft systems of the type described can be found in U.S. Pat. Nos. 4,787,899; 4,104,399; 5,219,355; and 5,275,622, which are incorporated herein by reference.

The actual function of delivering the graft may be accomplished by inflating a balloon of a catheter by introducing pressurized fluid into a lumen of the catheter from a source external to the patient. Inflation of the balloon applies a force to the graft and any attachment system supplied therein which extends radially and presses the graft and attachment system into the vessel wall just above and just below the aneurysm. When an attachment system is used, disengagement of the catheter from the graft also has been accomplished by taking advantage of the chemical properties of the material from which the attachment system is manufactured. For example, a prior art attachment system may be in the form of a coil of a nickel-titanium alloy, available under the trademark "NITINOL", that will expand radially upon being heated to a higher temperature. The longitudinal dimension of any attachment system used must account for any reduction in length that might result from radial expansion of the device. Other devices used to attach a graft to the aortic wall for AAA repair include intravascular stents of the type found in U.S. Pat. No. 4,733,665.

In order for a stent to be used most advantageously with a graft deployment system for treatment and repair of aneurysms, it is desirable for the stent to be composed of a biocompatible material, and to be simultaneously flexible enough to comply with the catheter or other element used to route the graft through the often tortuous vascular path to the site of the aneurysm and strong enough radially to maintain patency of the opening in the graft once delivered. The stent should be well suited to deployment by a delivery system that is not overly complex, and is reliable and easy to operate. Further it is desirable that the stent be expandable, so that upon application of a force or physical change from within sufficient to cause its radial expansion, it encourages affixation of itself and the graft to the aortic walls. Although various graft delivery systems have been proposed, none adequately provides all of the desirable features.

An important feature of any of the AAA repair devices includes the interface between an intravascular stent for attaching the system to the aorta, and the vascular graft which spans the aneurysm and provides a fluid-tight seal to prevent further injury. Specifically, the intravascular stent which provides the means for attachment is of the expandable type or self-expanding, expansion of which can be limited by the maximum diameter of the vascular graft. In other words, the vascular graft, made from a woven material (such as DACRON® and other polyester materials, or TEFLON®), has a maximum diameter that is generally not expandable. Thus, in those prior art systems where the stent overlaps the vascular graft, the expandable diameter of the stent is limited to the maximum outside diameter of the vascular graft. This could be a disadvantage if the vascular graft is not sized properly for a particular patient where it might be desirable to expand the stent, for fixation purposes, to a larger diameter than that of the vascular graft. Such prior art systems can be found for example in U.S. Pat. No. 5,316,023, in which about 50% of the length of the stent is overlapped by the end of the vascular graft.

What has been needed and has heretofore been unavailable is an apparatus for connecting the stent to the vascular graft which allows a high degree of flexibility for efficient advancement through tortuous passageways, which can be readily expanded from a relatively small delivery diameter (low profile) to a relatively large implanted diameter, and which provides a stent that can be radially expanded without interference from the maximum outer diameter of the vascular graft. Further, what has been needed is a design for a graft and stent assembly to be delivered in series (not coaxially) thereby minimizing the deployment diameter. The present invention meets these needs.

SUMMARY OF THE INVENTION

Briefly, and in general terms, the present invention provides for an apparatus to connect an intravascular stent to a vascular graft for use in repairing aortic aneurysms. In keeping with the invention, an intravascular stent is expandable from a first, delivery diameter, to a second implanted diameter. A vascular graft is folded along its longitudinal axis to provide a first diameter approximating the delivery diameter of the stent, and it has a second diameter approximating the implanted diameter of the stent. In a preferred embodiment, a flexible coupler has a first end and a second end which are attached to one end of the stent and vascular graft respectively.

In keeping with the invention, the coupler can be funnel-shaped, having a neck portion and a base portion. The neck portion has a smaller diameter than the base portion, with a tapered section in between. The neck portion of the coupler overlaps and is attached to one end of the stent so that the stent resides within the neck portion of the coupler and partially within the funnel section of the coupler. The vascular graft fits within the base portion of the coupler and is attached thereto by various means. In the preferred embodiment, the stent is attached to the neck portion of the coupler by suturing or by bonding. Similarly, the intravascular graft is attached to the base portion of the coupler by suturing, bonding or a dipping process. Upon implanting the stent-coupler-graft assembly in a body lumen, the stent and the graft preferably do not overlap. However, under some circumstances the stent and graft may slightly overlap.

Other means of attaching the stent and graft to the coupler include a mechanical connection such as a tab portion on the stent that will pierce the neck portion of the coupler and provide a secure attachment means. Other attachment means include a plurality of fibers within said coupler and extending from the neck portion and the base portion. The fibers extending from the neck portion of the coupler are attached to the stent while the fibers extending from the base portion are attached to the graft. Upon expanding the stent and unfolding the graft from their first, delivery diameter, to their second enlarged implanted diameter, the coupler will expand and the fibers will provide extra safety in the connection of the stent to graft.

In another preferred embodiment, the coupler is expandable and can elongate up to 500% and is made from a biocompatible material. The coupler can be made from highly elastic materials taken from the group of elastic materials of polyurethane, silicone copolymers, latex, SEB's and their associated families.

These and other aspects and advantages of the invention will become apparent from the following detailed description, and the accompanying drawings, which illustrate by way of example features of the invention.

DETAILED DESCRIPTION OF THE PREFERRED EMBODIMENTS

In keeping with the invention, it is desirable to connect a stent and a vascular graft to provide a flexible connection that is reliable and does not limit the expanded diameter of the stent to the outside diameter of the expanded vascular graft. It is also desired to provide a graft and stent assembly where the graft and stent do not overlap, thereby minimizing the delivery diameter (profile) of the assembly. Thus, a medical device for connecting an intraluminal stent and a vascular graft is provided.

Figure 1:
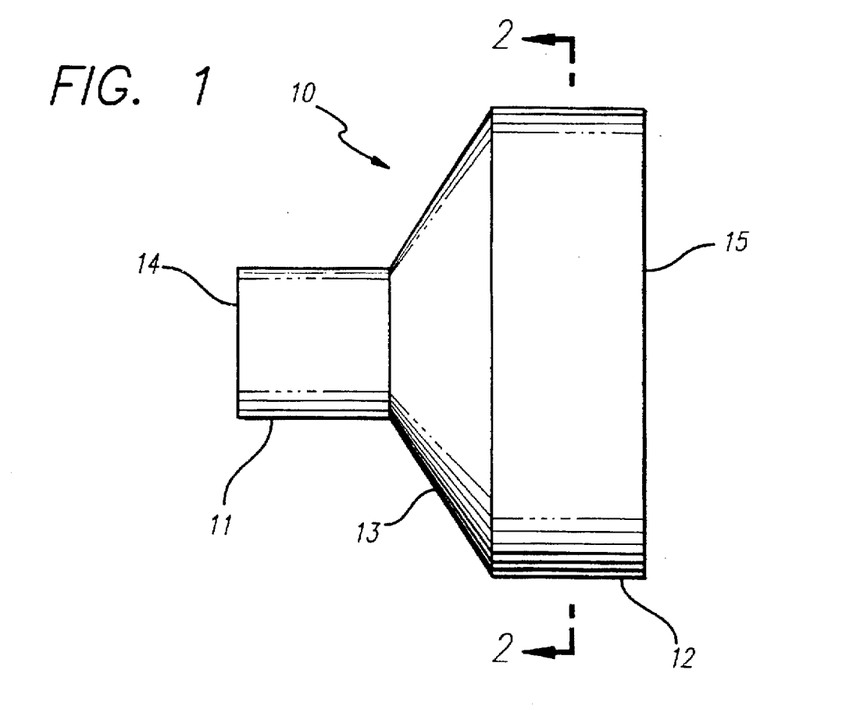
FIG. 1 is a plan view of a coupler having a funnel shape, including a neck portion and a base portion.

Referring to FIG. 1, in a preferred embodiment of the invention, a coupler 10 is provided and has a neck portion 11 and a base portion 12. A tapered portion 13 connects neck portion 11 and base portion 12. As will be described more fully herein, coupler 10 has a first end 14 and a second end 15 which interface with an intravascular stent and a vascular graft.

Figure 2:
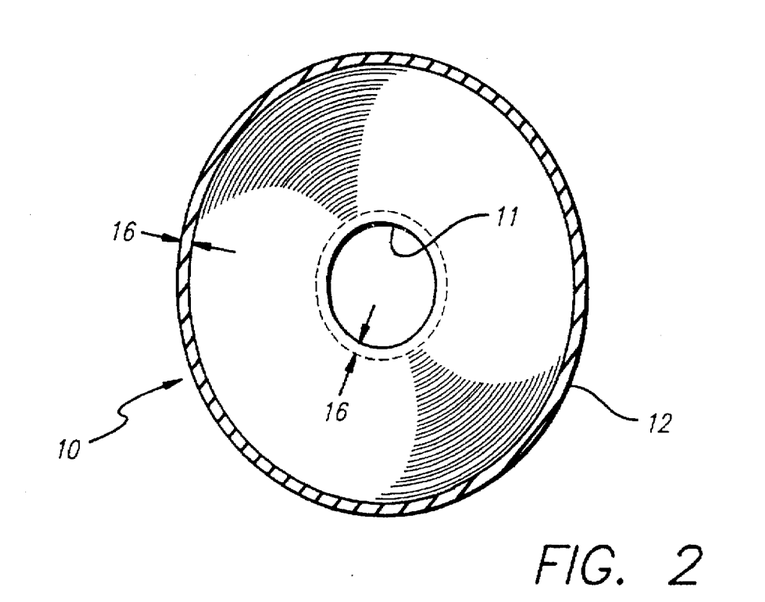
FIG. 2 is a cross-sectional view of the coupler of FIG. 2 taken along lines 2—2 depicting the thickness of the walls of the coupler.

In keeping with the invention, and as depicted in FIGS. 1 and 2, coupler 10 is formed from an elastic material which allows it to elongate up to 500%. Coupler 10 is hollow and has a wall thickness 16 in the range of 0.0003 inches to 0.010 inches. The coupler can be formed from any number of highly elastic materials which include polyurethanes, silicone copolymers latex, and polysiloxane modified ethylene/ butylene-styrene block copolymers (SEB's) and their associated families. An example of a medical grade polymer having about a ten-year history of human use is CARDIO-THANE 51 Polymer. It is a complex blend of polyurethane, silicone and the copolymer of both, and is available from Kontron Instruments, Everett, Mass. Another medical grade polymer suitable for use in making coupler 10 is CHRONOFLEX-AR, available from Polymedica, Inc., Woburn, Mass. Coupler 10 can be manufactured by dip coating or extruding through known methods.

Figures 3, 4:
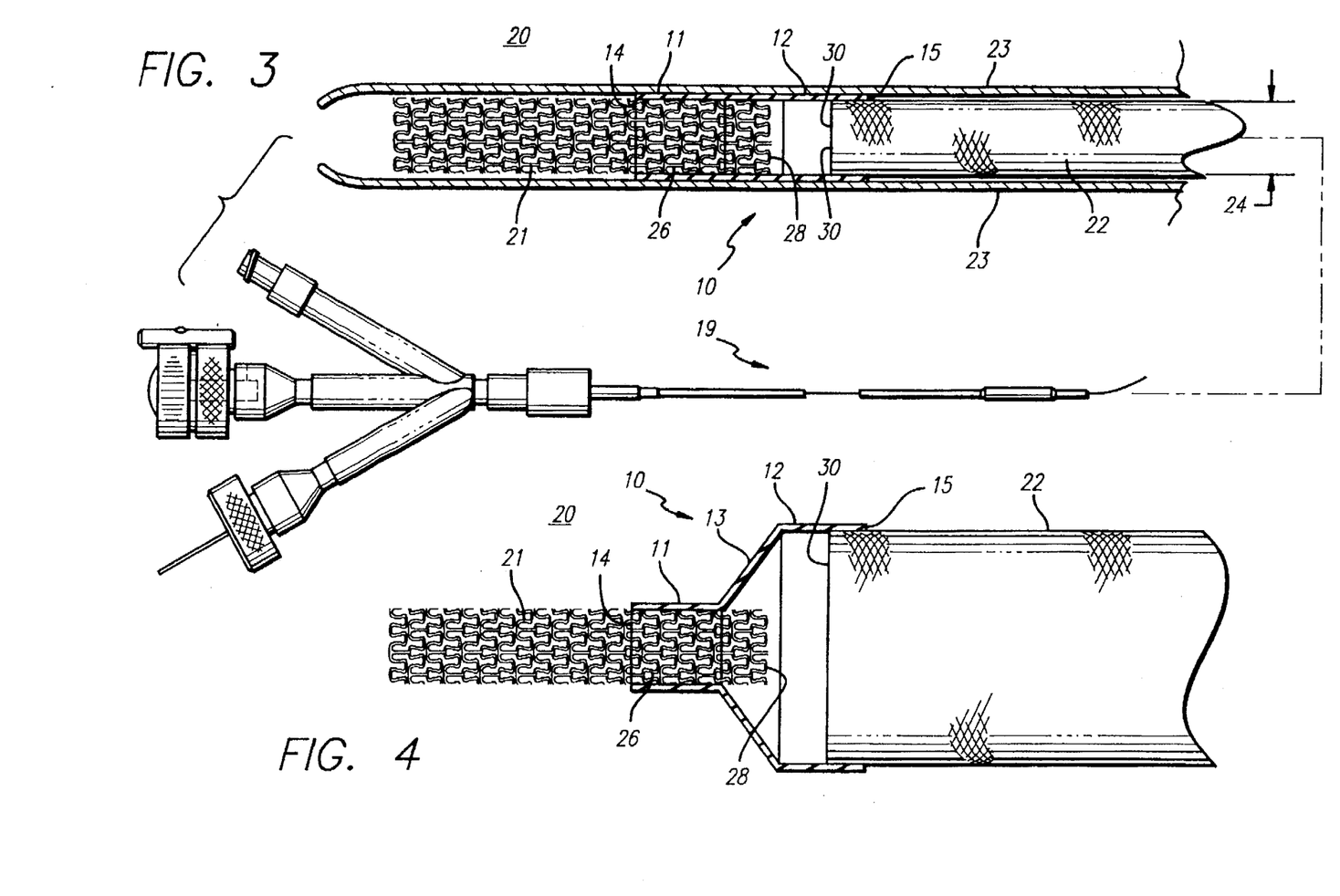
FIG. 3 is a plan view, partially in cross-section, of the coupler attached at its one end to an intravascular stent and at its other end to a vascular graft, and a balloon catheter for delivering the stent-coupler-graft assembly.
FIG. 4 is a plan view, partially in cross-section, depicting the assembly of FIG. 3 in which the graft has been allowed to unfold to its maximum, implantable diameter, while the stent and the neck and funnel portions of the coupler remain unexpanded.
Figure 5:
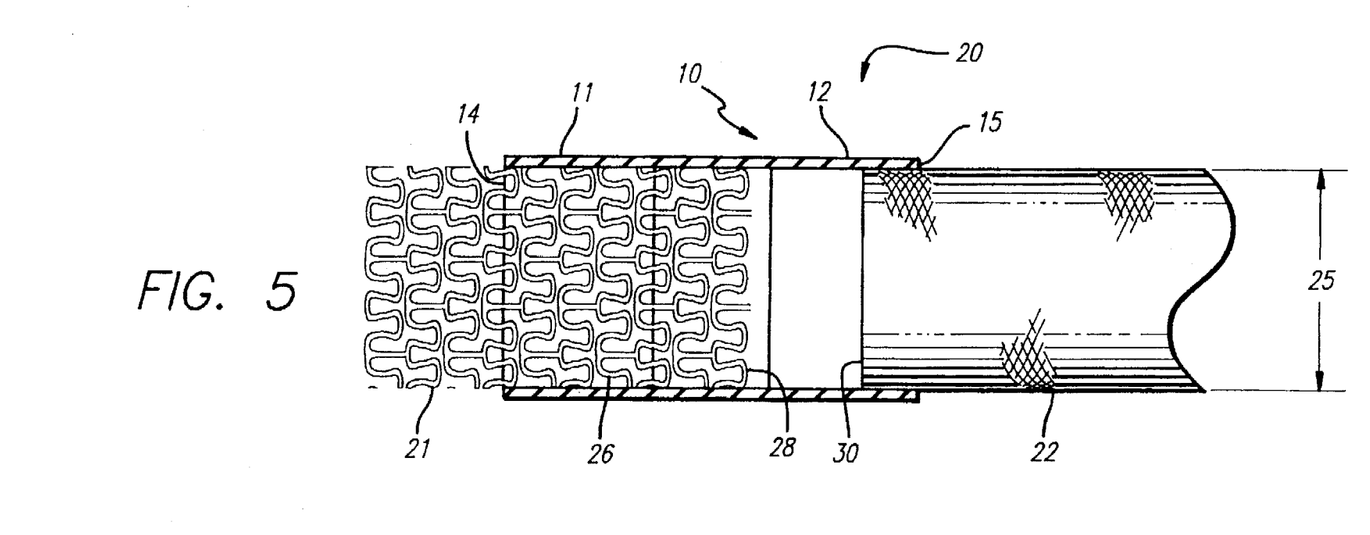
FIG. 5 is a plan view of the assembly of FIGS. 3 and 4 depicting the stent, coupler and graft in their fully expandable implantable diameter.

Turning to FIGS. 3–5, the coupler of the present invention is shown as it is incorporated in a stent-coupler-graft assembly 20. Generally, the stent-coupler-graft assembly is mounted on a conventional balloon catheter 19 for delivering assembly 20 through the vascular system. Under normal circumstances, the assembly 20, as mounted on a balloon catheter 19, is introduced into the patient's vasculature percutaneously by a femoral approach and it is routed to the area of an aortic aneurysm, being viewed by fluoroscopy and/or IVUS (ultrasound) to assist the physician in proper positioning. Examples of suitable balloon catheters adaptable to deliver the present invention can be found in U.S. Pat. Nos. 4,323,071; 4,573,470; 4,582,181; 4,641,654; 4,661,094; 4,877,031; 5,219,355; and 5,275,622, which are incorporated herein by reference.

The stent-coupler-graft assembly 20 includes an intraluminal stent 21 having any number of configurations which may include attachment hooks (not shown) to assist in attaching the stent to the aortic wall after the stent has been expanded. Other types of stents may be used with the present invention, including expandable stents without hooks or self-expanding stents with or without attachment hooks. The stents that can be used with the present invention can be made from metals or polymers and have numerous configurations.

Assembly 20 also includes vascular graft 22 which generally includes a hollow tubular graft made from woven material, which is a lattice-like or open weave structure which promotes rapid endothelial tissue growth on and through the graft structure once it has been deployed. Known tubular graft materials include DACRON® and TEFLON®, as well as other biocompatible materials. Although graft 22 is depicted as a tubular-shaped member, it is representative only and can in fact have other configurations such as bifurcated grafts, pleated grafts, or grafts having longitudinal supporting members.

Generally, the stent-coupler-graft assembly 20, after it is mounted on a balloon catheter 19, has a sheath 23 overlying the assembly to help hold it on the balloon catheter and to protect the patient's vasculature from any rough edges on the assembly. Further, sheath 23 will protect the distal end of assembly 20, and primarily the distal end of stent 21, from catching on the patient's vasculature, especially in any tight turns near the aortic bifurcation.

In a preferred embodiment, as depicted in FIG. 3, stent 21 has a first delivery diameter, as does coupler 10 and graft 22. With this reduced, low profile diameter, assembly 20 passes easily through the patient's vasculature. The low profile, reduced diameter also permits a smaller entry through the femoral artery which reduces the likelihood of complications during the initial cut-down and during any postoperative closure of the artery. Since coupler 10 is both flexible and elastic, it assumes the smallest diameter of stent 21 and graft 22. Generally, in order to achieve the smallest delivery profile, graft 22 is folded along its longitudinal axis.

As is shown in FIG. 4, sheath 23 has been removed and graft 22 has been unfolded from its delivery diameter to a second, implanted diameter 25. The implanted diameter is slightly smaller than the inside diameter of the healthy aorta which is on either end of the aneurysm.

As depicted in FIG. 5, stent 21 has been expanded from its first, delivery diameter 24 to its second, implanted diameter 25. The implanted diameter 25, as depicted in FIG. 5, is substantially the same for coupler 10, stent 21 and graft 22, and is primarily dictated by the inside diameter of the patient's aorta. It is important that the treating physician correctly approximate the inside diameter of the aorta so that graft 22, when unfolded to implanted diameter 25, substantially approximates and is slightly smaller than the inside diameter of the patient's aorta. The implanted diameter 25 of stent 21 may be, with some stent configurations, slightly larger than implanted diameter 25 for graft 22. Under some circumstances, it may be desirable to utilize the balloon portion of a catheter to expand stent 21 so that it presses into the inner walls of the patient's aorta to insure that attachment to the aortic wall is secure. Further, some stents 21 will have anchoring hooks, barbs, or rough outer surfaces that penetrate the aortic wall so that the implanted diameter 25 of stent 21 is slightly larger than the implanted diameter of graft 22.

Given the highly elastic nature of coupler 10, it is able to accommodate varying diameters of stent 21 and graft 22 as seen in FIG. 4.

In further keeping with the invention, as depicted in FIGS. 3–5, stent outer surface 26 is inserted within neck portion 11 of coupler 10. Since coupler 10 is highly elastic, it fits tightly over stent outer surface 26 and is attached thereto by bonding with known adhesives, or suturing with a suitable biocompatible material.

Similarly, and with further reference to FIGS. 3–5, distal end 30 of graft 22 is attached to base portion 12 of coupler 10. As with the stent attachment, graft 22 may be bonded or sutured to base portion 12 to firmly attach graft 22 to coupler 10. As another form of attachment, coupler 10 is impregnated into the matrix/fibers of the graft 22 material by a dipping process. Importantly, graft 22 will be tightly folded along its longitudinal axis to its reduced profile delivery diameter as shown in FIG. 3, and due to the elastic nature of coupler 10, it will assume the same folded configuration where it is attached to distal end 30 of the graft.

In one preferred embodiment of the invention as depicted in FIGS. 3–5, it is contemplated that stent 21 is bonded to coupler 10 such that it does not overlap or abut any portion of graft 22, also attached to coupler 10. When the graft-coupler-stent assembly 20 is mounted on a balloon catheter for delivery, coupler 10 will be straightened in a longitudinal direction so that the entire assembly 20 has a low profile, as depicted in FIG. 3. This also assists in placing sheath 23 over assembly 20 to maintain a low profile for intraluminal delivery. Thereafter, sheath 23 is withdrawn from assembly 20 as seen in FIG. 5. As seen in FIG. 5, stent 21 is fully expanded, graft 22 has been unfolded, and coupler 10, due to its elastic nature, conforms to the shape of the stent and graft.

Alternatively, in another embodiment, it may be possible that stent 21 and graft 22, when implanted, will slightly overlap. Thus, coupler 10 will shrink longitudinally somewhat due to its elastic nature, drawing stent 21 and graft 22 toward each other so that stent 21 at its proximal end 28 will reside within the distal end 30 of graft 22. Even if this occurs, it will not impair the ability to expand stent 21 to its maximum diameter for a positive attachment to the aortic wall.

Figure 6:
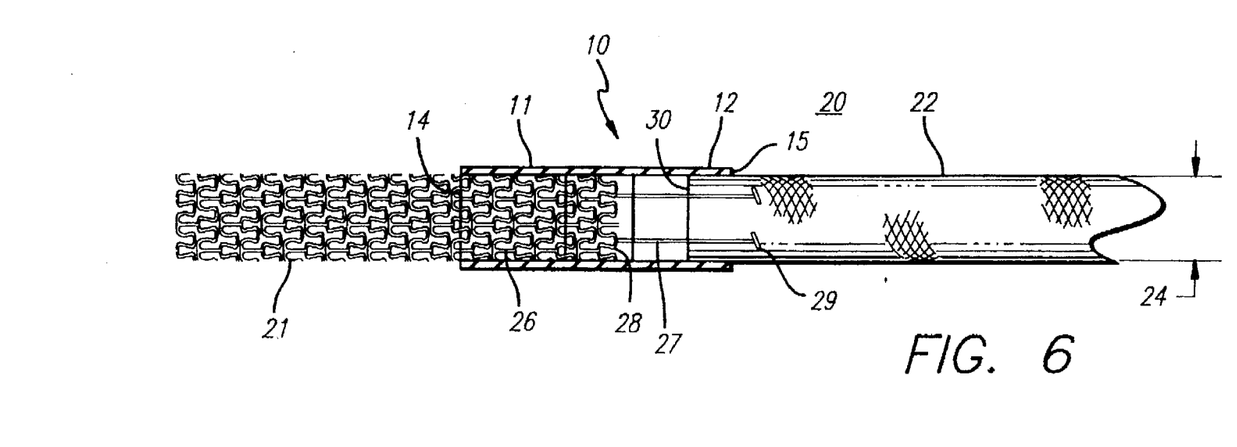
FIG. 6 is a plan view, partially in cross-section, of the coupler attached at its one end to an intravascular stent by attachment tabs.
Figures 7, 8:
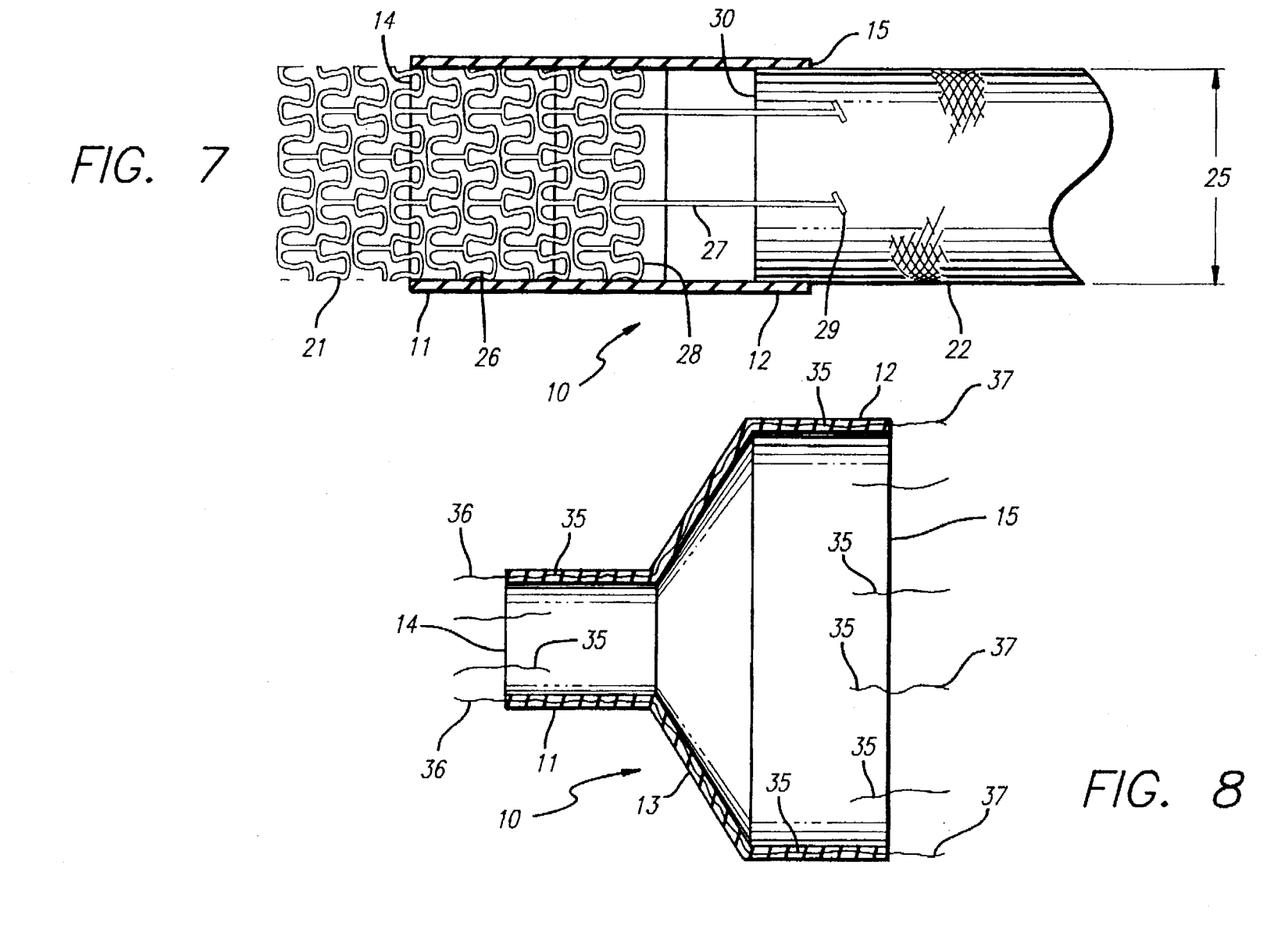
FIG. 7 is a plan view of the assembly of FIG. 6 depicting the stent attached to the coupler by attachment tabs, and the entire assembly in its fully expandable implanted diameter.
FIG. 8 is a cross-sectional view of the coupler depicting an alternative embodiment wherein fibers are embedded in the walls of the coupler for attachment to the stent at one end and to the vascular graft at the other end of the coupler.

In an alternative embodiment shown in FIGS. 6–7, tabs 27, extending from the proximal end 28 of the stent, are used to attach stent 21 to graft 22, with coupler 10 overlapping a portion of the stent and graft. Each of tabs 27 has a T-member 29 that is inserted through the distal end 30 of graft 22 to attach tab 27 to the graft. For ease of attachment, T-member 29 can be turned so that it is parallel to tab 27 and then inserted into graft 22. T-member 29 is then turned 90° so that it is perpendicular to tab 27, thereby forming T-member 29 and attaching stent 21 to graft 22.

In another alternative attachment means, as depicted in FIG. 8, coupler 10 has a plurality of fibers 35 interwoven into the walls of coupler 10. The fibers 35 extend from first end 14 of coupler 10 and from second end 15 and can be made from a polymeric material that preferably is non-stretchable. Distal fibers 36 extend from first end 14 of coupler 10 and are attached to stent 21 by bonding or other suitable means. Proximal fibers 37 extend from second end 15 of coupler 10 and are attached to graft 22 by bonding, or knotting, or they can be woven into graft 22.

Figure 9:
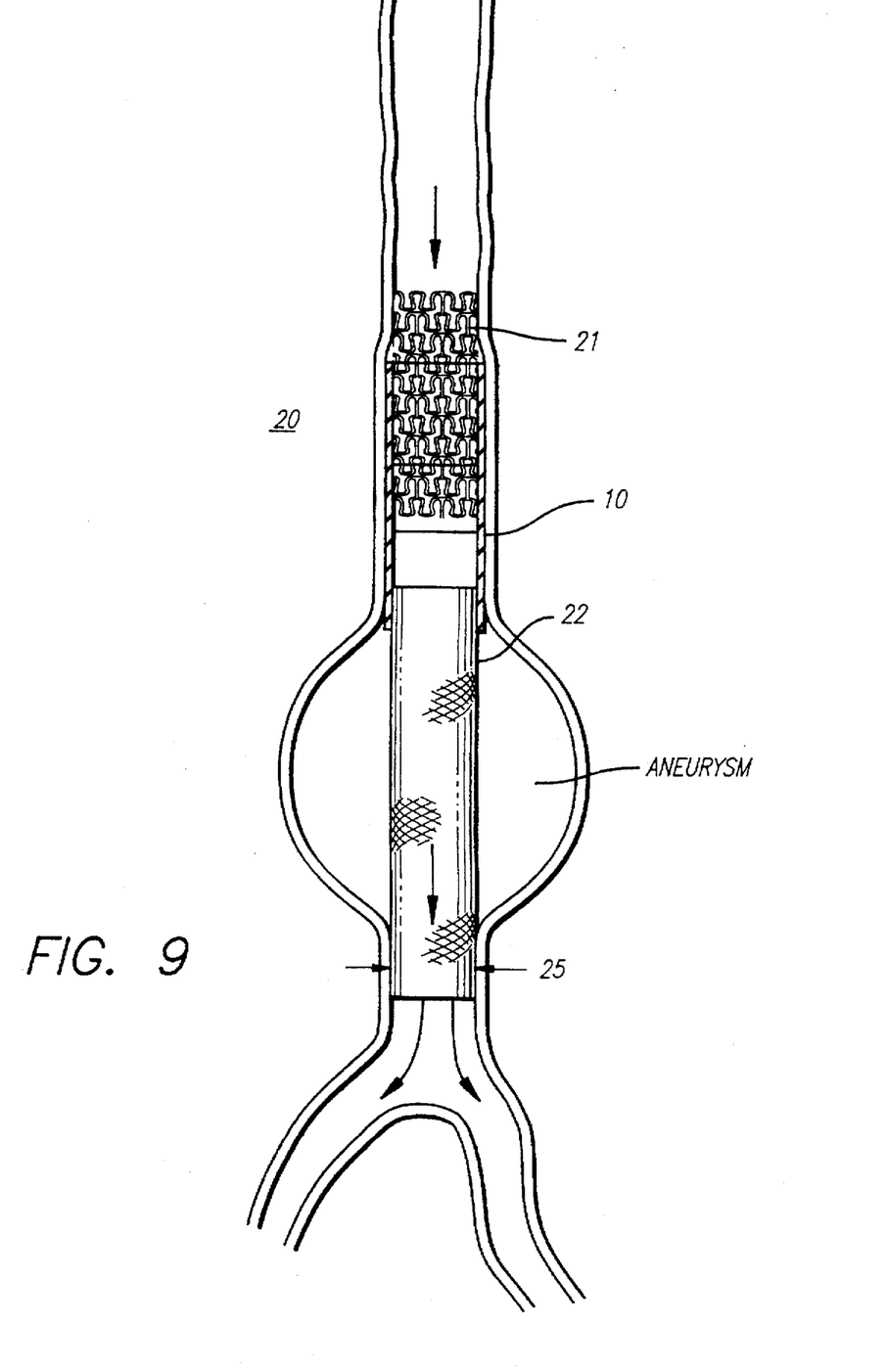
FIG. 9 is a cross-sectional view of a stent, coupler and vascular graft connected together and implanted in an aorta where the vascular graft spans the aneurysm and provides a fluid-tight seal to prevent blood from entering the aneurysm.

Turning to FIG. 9, stent-coupler-graft assembly 20 is shown implanted in a patient's aorta where graft 22 spans the aneurysm. As described previously, assembly 20 is delivered to the area of the aneurysm (or embolism) by a balloon catheter 19 by a femoral approach. Assembly 20 is positioned so that graft 22 spans the aneurysm, and stent 21 is then expanded by the balloon portion of the catheter into healthy tissue distal of the aneurysm. Since coupler 10 is of a highly elastic nature, it allows some flexibility between stent 21 and graft 22. It is also contemplated that coupler 10 will have a tendency to draw stent 21 and graft 22 toward each other as the stent and graft are expanded to implanted diameter 25. When assembly 20 is in its fully opened position and implanted diameter, the arrows in FIG. 9 depict the direction of blood flow through the artery.

While the invention has been illustrated and described herein in terms of its use as an endoprosthesis for implanting a graft to treat an aneurysm, it will be apparent to those skilled in the art that the stent-coupler-graft assembly can be used in other instances in other vessels of the body. Because the coupler of the present invention permits the flexible attachment of a stent and a graft, and is highly elastic, it is particularly well suited to implantation in almost any vessel where such devices can be used, especially in vessels where a low profile or extreme tortuosity is encountered.

In the foregoing description, statements concerning specific dimensions are given by way of example, and it should be apparent to one of ordinary skill in the art that other similar dimensions may also be suitable according to the principles of the invention. Further, it is also apparent that specific references to materials used in forming various aspects of the invention can also be substituted with equivalent materials. It will therefore be apparent from the foregoing that while particular forms of the invention have been illustrated and described, various modifications can be made without departing from the spirit and scope of the invention. Accordingly, it is not intended that the invention be limited except as by the appended claims.

What is claimed is:

1. An assembly for connecting a stent and a vascular graft, comprising:

an intravascular stent that is expandable from a delivery diameter to an implanted diameter;

a vascular graft having a folded diameter approximating said delivery diameter of said stent, and having an unfolded diameter approximating said implanted diameter of said stent;

a flexible coupler having a first end attached to said stent and a second end attached to said graft, said stent, said graft and said coupler forming a stent-coupler graft assembly that remains connected during delivery through a body lumen, wherein said stent-coupler-graft assembly has a substantially uniform reduced profile formed by contracting said stent and folding said graft, said stent-coupler-graft assembly remaining connected after deployment of said stent to said implanted diameter and said graft to said unfolded diameter, with no portion of said graft overlapping said stent.

2. The assembly of claim 1, wherein said coupler is funnel-shaped.

3. The assembly of claim 2, wherein said first end of said coupler is expandable up to a diameter of approximately 0.800 inches, and said second end of said coupler is unexpanded and at rest at a diameter of approximately 0.800 inches.

4. The assembly of claim 1, wherein said coupler material can elongate up to 500%.

5. The assembly of claim 1, wherein said coupler is made from a biocompatible material.

6. The assembly of claim 5, wherein said coupler is made from highly elastic materials, taken from the group of elastic materials of polyurethane, silicone copolymers, latex, and polyseloxane modified ethylene/butylene-styrene block copylymers (SEB's).

7. The assembly of claim 1, wherein said coupler has a wall thickness in the range of 0.0003 inches to 0.010 inches.

8. The assembly of claim 1, wherein said coupler provides a fluid-tight seal between said stent and said graft.

9. The assembly of claim 1, wherein said graft is bonded to said second end of said coupler.

10. The assembly of claim 1, wherein said stent is bonded to said first end of said coupler.

11. The assembly of claim 1, wherein said stent has a plurality of T-members extending from one end, said T-members being adapted for attachment to said first end of said graft.

12. The assembly of claim 1, wherein said first end of said coupler is sutured to said stent, and said second end of said coupler is attached to said graft by a dipping process.

13. The assembly of claim 1, wherein a plurality of fibers are woven into said coupler, said fibers extending from said first end and from said second end of said coupler, wherein said fibers extending from said first end are attached to said stent, and said fibers extending from said second end are attached to said graft.

14. The assembly of claim 13, wherein said fibers are made from a suture material.

15. The assembly of claim 14, wherein said fibers are bonded to said stent and said graft.

16. A method of repairing a body passageway, including an intravascular stent that is expandable from a first, delivery diameter to a second, implanted diameter, a vascular graft having a diameter approximating said implanted diameter of said stent, and a flexible coupler adapted to attach said intravascular stent and said vascular graft to form a stent-coupler-graft assembly, the method comprising:

attaching said stent to one end of said coupler and attaching said graft to the opposite end of said coupler;

mounting the stent-coupler-graft assembly on a balloon catheter;

reducing the profile of the stent-coupler-graft assembly to a first diameter by crimping said stent onto the balloon portion of said catheter, and folding said graft onto said catheter, to reduce the overall profile so that said stent-coupler-graft assembly has a substantially uniform first delivery diameter;

inserting said stent-coupler-graft assembly on said balloon catheter assembly percutaneously and transporting through the body passageway;

deploying said stent-coupler-graft assembly by expanding said stent to an enlarged, second diameter and unfolding said graft; and withdrawing said balloon catheter assembly from the body passageway.

17. The method of claim 16, wherein said coupler expands up to 500% when said stent is expanded.

18. The method of claim 16, wherein said stent and said graft remain spaced apart during delivery and implanting of said stent-coupler-graft assembly.

* * * * *